United States Patent [19]

Steen

[11] Patent Number: 5,092,989
[45] Date of Patent: Mar. 3, 1992

[54] SHEATH FLUID FILTERING IN A CLOSED-CYCLE FLOW CYTOMETER SYSTEM

[75] Inventor: Harald B. Steen, Oslo, Fed. Rep. of Germany

[73] Assignee: Skatron A/S, Tranby, Norway

[21] Appl. No.: 597,667

[22] Filed: Oct. 17, 1990

[30] Foreign Application Priority Data

Oct. 19, 1989 [NO] Norway .................................. 894161

[51] Int. Cl.$^5$ ............................................. B01D 35/00
[52] U.S. Cl. ...................................... 210/85; 210/167;
210/195.1; 210/196; 210/257.1; 210/259;
210/416.1; 210/489; 210/492; 422/73;
422/82.08; 435/287; 435/311; 436/63; 436/172

[58] Field of Search .............. 210/420, 85, 167, 195.1,
210/196, 257.1, 259, 416.1, 489, 492, 502.1;
422/73, 81, 82, 82.07, 82.08, 101; 435/287, 311;
436/63, 172

[56] References Cited

U.S. PATENT DOCUMENTS 4,844,610  7/1989  North .................................... 356/73

Primary Examiner—Robert A. Dawson
Assistant Examiner—Sun Uk Kim
Attorney, Agent, or Firm—Cushman, Darby & Cushman

[57] ABSTRACT

A system for filtering, purification, and recirculation of the sample carrier water in a flow cytometer. After running through the flow chamber of the flow cytometer, the water, including the sample, is passed through physical and chemical filters to remove cells, cell debris and other particulate matter as well as dyes, before the water is recycled through the instrument as carrying, or sheath fluid for subsequent samples.

2 Claims, 1 Drawing Sheet

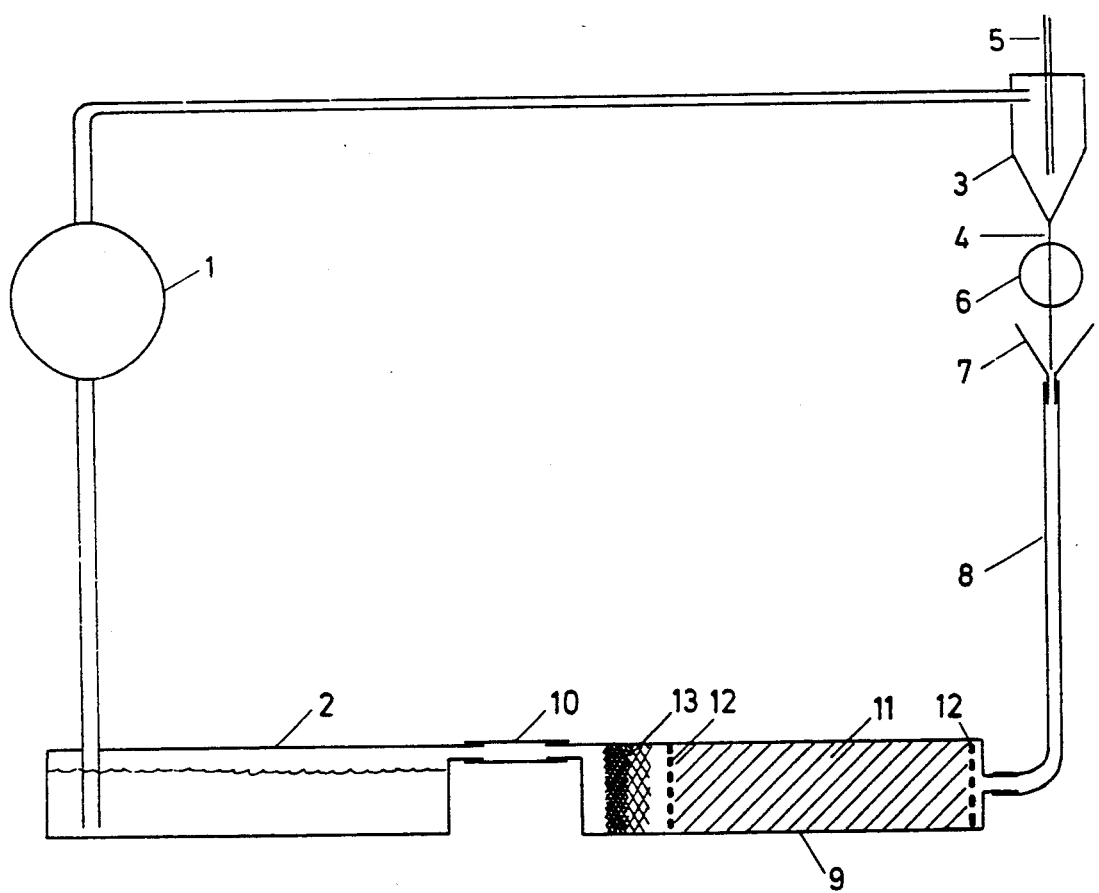

SHEATH FLUID FILTERING IN A CLOSED-CYCLE FLOW CYTOMETER SYSTEM

BACKGROUND OF THE INVENTION

The present invention relates to a system for purification and recirculation of water passing through the flow chamber of a flow cytometer.

A flow cytometer is an instrument for measuring the fluorescence and light scattering of individual biological cells in large numbers. The measurement is carried out when the cells are passed one by one through the focus of an intense source of light which excites fluorescent dyes in the cells. Thus, the fluorescence intensity is a measure of the particular constituent of the cell which binds the fluorescent dye. The intensity of the scattered light is primarily a measure of the size of the cell. The fluorescence and scattered light are collected by appropriate optics and detected by means of separate photomultiplier tubes or other sensitive light detectors. The detectors transform the light pulses into equivalent electrical pulses which are subsequently digitized, stored and classified in a computer.

The cells are carried through the excitation focus by a laminar flow of water having a cross-section of microscopic dimensions. This carrying water, which is commonly termed "sheath fluid", is fed into a conical flow chamber under a pressure of the order of 1 kg/cm$^2$. The orifice of the flow chamber, which typically has a cross-section of the order of 100 $\mu$m, leads either into air where the water forms a cylindrical jet or into a tube passing through the excitation focus. The sample, which is usually a suspension of cells, is introduced into the flow chamber through a tube along the center of the flow chamber. Hence, the cells are confined to the central core of the flow through the excitation focus.

The amount of sheath fluid passing through the flow chamber is about 10 ml/min, which means that a flow cytometer consumes on the order of 5 liters per day. Hence, most flow cytometers have a water reservoir of about that volume. This reservoir adds significantly to the weight and volume of the instrument. Especially in instruments intended for field use, it is important to reduce this volume as much as possible. In instruments designed for use in spaceships, such a reduction is of course essential. There is an increasing demand for field instruments which can run unattended for long periods of time.

The water used as sheath fluid must be of high purity. Usually one uses distilled water which is subsequently passed through a filter having a pore size of 0.2 $\mu$m. Water of such quality is not readily available in all laboratories using flow cytometry.

Another problem in the use of flow cytometers is that some of the fluorescent dyes used to stain cells, and especially dyes used to stain the DNA, i.e. the genetic material, are highly mutagenic and/or carcinogenic. The waste water from flow cytometers should therefore not be drained into the public sewer, as is now the case. On the other hand it is expensive to dispose of such large volumes of water in a more responsible way.

SUMMARY OF THE INVENTION

The present invention solves these problems by devising a way by which the water is filtered and purified to be reused again and again. Thus, the total volume of water in a flow cytometer can be reduced by two orders of magnitude and the volume of the waste to be disposed of is reduced correspondingly.

The system according to the invention provides: a) a pump driving water from a reservoir into the flow chamber and through the excitation focus; and b) a composite filter through which the water leaving the focus by way of a funnel and a tubing runs back into the reservoir through the tubing.

According to a further feature of the system, said composite filter contains a chemically active material which absorbs the dyes used to stain cells for flow cytometry and mechanical filters which remove cells and other particulate material from the water.

BRIEF DESCRIPTION OF THE FIGURE

The invention is now to be described with reference to the attached drawing FIGURE, which illustrates a preferred, nonlimitative embodiment of the invention.

DETAILED DESCRIPTION

The system comprises a pump 1 which pumps water from a reservoir 2 under constant pressure to the flow chamber 3 of the flow cytometer and thereby produces the laminar jet of water 4 which carries the cells through the excitation focus 6. The cell suspension is introduced into the flow through a thin tube 5 along the axis of the flow chamber. When the water has passed through the excitation focus 6 it flows into a funnel 7 leading through a tubing 8 into a composite filter 9. After passing through this filter, the water flows through the tubing 10 back to the reservoir 2.

The composite filter 9 has a dual function: it removes cells, cell debris, and other particulate matter from the water, and it absorbs the fluorescent dyes of the sample. The composite filter 9 may have the form of a horizontal tube through which the water is driven by the pressure exerted by the liquid level in the tube 8. The outlet of the filter 9 is in such a position as to allow any air to escape.

The main part of the filter 9 is filled with a chemically active material 11, such as active carbon, which is kept in place by a fine mesh of stainless steel 12 on either side. In order to remove particulate material, including carbon particles, the chemical filter 11 is followed by several mechanical filters 13 having decreasing pore size in the direction of the flow. The smallest pore size may typically be around 0.2 $\mu$m.

The filter 9 has fittings at both ends so that it can easily be disconnected for replacement. Thus, once the filter is saturated with dyes and particulate material, it can be disposed of without exposure of its contents to the surroundings.

As an example, a composite filter, containing about 50 ml of active carbon, will absorb an amount of dyes corresponding to about 10,000 typical cell samples. Hence, a filter can be used for several months before renewal. The total volume of water in the entire system can be about 100 ml. To avoid infection and growth of algae and other microorganisms in the system, a biocide, such as sodium azide, may be added to the water.

Having described my invention, I claim:

1. Apparatus for providing sheath fluid filtering in a closed cycle flow cytometer system, comprising:
    a flow cytometer comprising a flow chamber having a longitudinal axis;
    a reservoir for water;

a pump provided in a first tube arranged for pumping water from said reservoir into said flow chamber so as to produce a laminar jet of water;

a tube entering said flow chamber along said axis for introducing a suspension of cell sample material, including at least one of cells, cell debris, particulate matter and cell-staining dye into said laminar jet of water in said flow chamber;

a second tube communicating an outlet of said flow chamber with said reservoir for returning water to said reservoir;

said cytometer further including an exitation focus located in said second tube between said flow chamber and said reservoir, and arranged so that the laminar jet of water carries the cell sample material through said exitation focus; and a composite filter interposed in said second tube, between said exitation focus and said reservoir, and arranged for filtering said cell sample material from water returning through said second tube to said reservoir.

2. The apparatus of claim 1, wherein:

said composite filter includes a body of absorbent for absorbing said dye, and a plurality of successively finer pore mechanical filters for filtering said cells, cell debris and particulate matter from said water returning through said second tube to said reservoir.

* * * * *